(12) United States Patent
Pujar

(10) Patent No.: US 10,349,854 B2
(45) Date of Patent: Jul. 16, 2019

(54) METHOD AND APPARATUS FOR ELECTROPHYSIOLOGY CATHETER SCHEME CONFIGURATION

(71) Applicant: Chandrashekhar Pujar, Karnataka (IN)

(72) Inventor: Chandrashekhar Pujar, Karnataka (IN)

(73) Assignee: SIEMENS HEALTHCARE GMBH, Erlangen (DE)

( * ) Notice: Subject to any disclaimer, the term of this patent is extended or adjusted under 35 U.S.C. 154(b) by 1163 days.

(21) Appl. No.: 14/626,693

(22) Filed: Feb. 19, 2015

(65) Prior Publication Data

US 2016/0242666 A1  Aug. 25, 2016

(51) Int. Cl.
| | |
|---|---|
| *A61B 5/044* | (2006.01) |
| *A61B 6/12* | (2006.01) |
| *A61B 5/042* | (2006.01) |
| *A61B 5/00* | (2006.01) |
| *A61B 6/00* | (2006.01) |
| *G16H 40/63* | (2018.01) |
| *G06F 19/00* | (2018.01) |

(52) U.S. Cl.
CPC ............ *A61B 5/0422* (2013.01); *A61B 5/044* (2013.01); *A61B 5/7435* (2013.01); *A61B 6/12* (2013.01); *A61B 6/503* (2013.01); *G06F 19/00* (2013.01); *G16H 40/63* (2018.01)

(58) Field of Classification Search
CPC .............................. A61B 5/743; A61B 5/7435
See application file for complete search history.

(56) References Cited

U.S. PATENT DOCUMENTS

| | | | |
|---|---|---|---|
| 8,382,706 B2 | 2/2013 | Nekich et al. | |
| 8,725,241 B2 | 5/2014 | Ramanathan et al. | |

*Primary Examiner* — Mark Bockelman
(74) *Attorney, Agent, or Firm* — Lempia Summerfield Katz LLC

(57) ABSTRACT

A method and an apparatus for electrophysiology catheter scheme configuration are disclosed. The method includes providing an interactive image of a heart to a user and receiving a user input of a type of catheter and a number of electrodes corresponding to the catheter. A pictorial representation of the catheter positioned inside the interactive image of the heart is generated according to the type of catheter. A pictorial representation of the electrodes as markers on the pictorial representation of the catheter is generated depending on the number of electrodes. Slot numbers of a catheter input pod are mapped to the corresponding electrodes of the catheter that are to be connected to the catheter input pod depending on the type of catheter. Intracardiac electrogram (ICEG) signal labels are assigned depending on the type of catheter, and the ICEG signal labels are marked on the interactive image of the heart to create the electrophysiology catheter scheme.

15 Claims, 9 Drawing Sheets

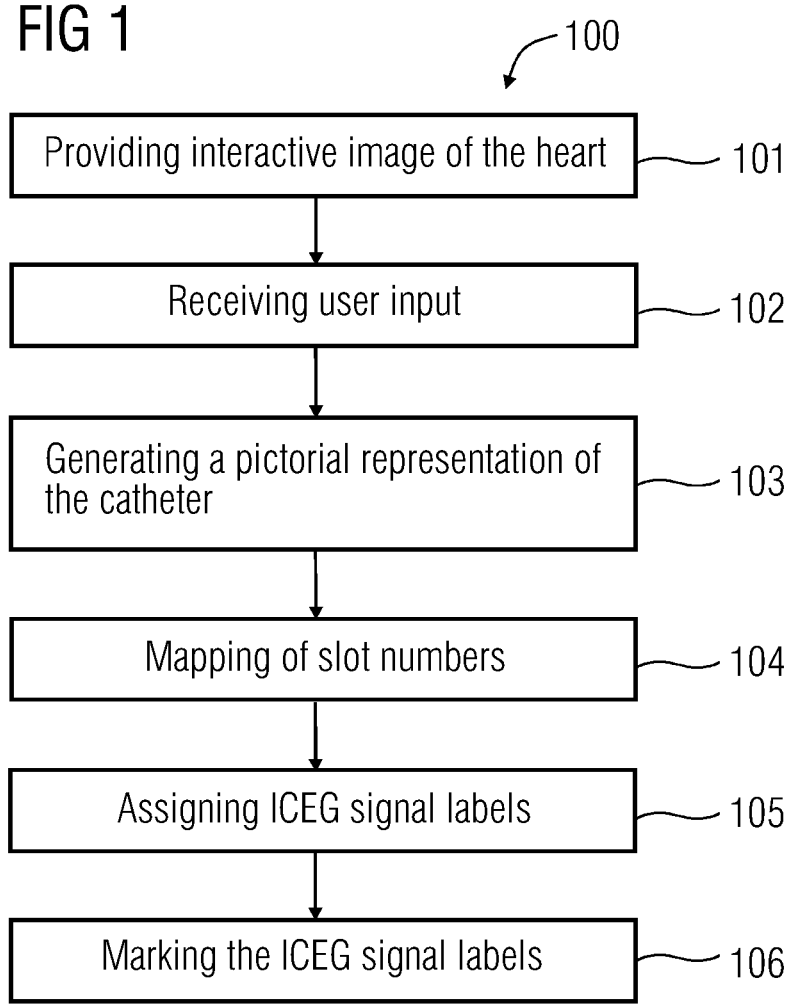

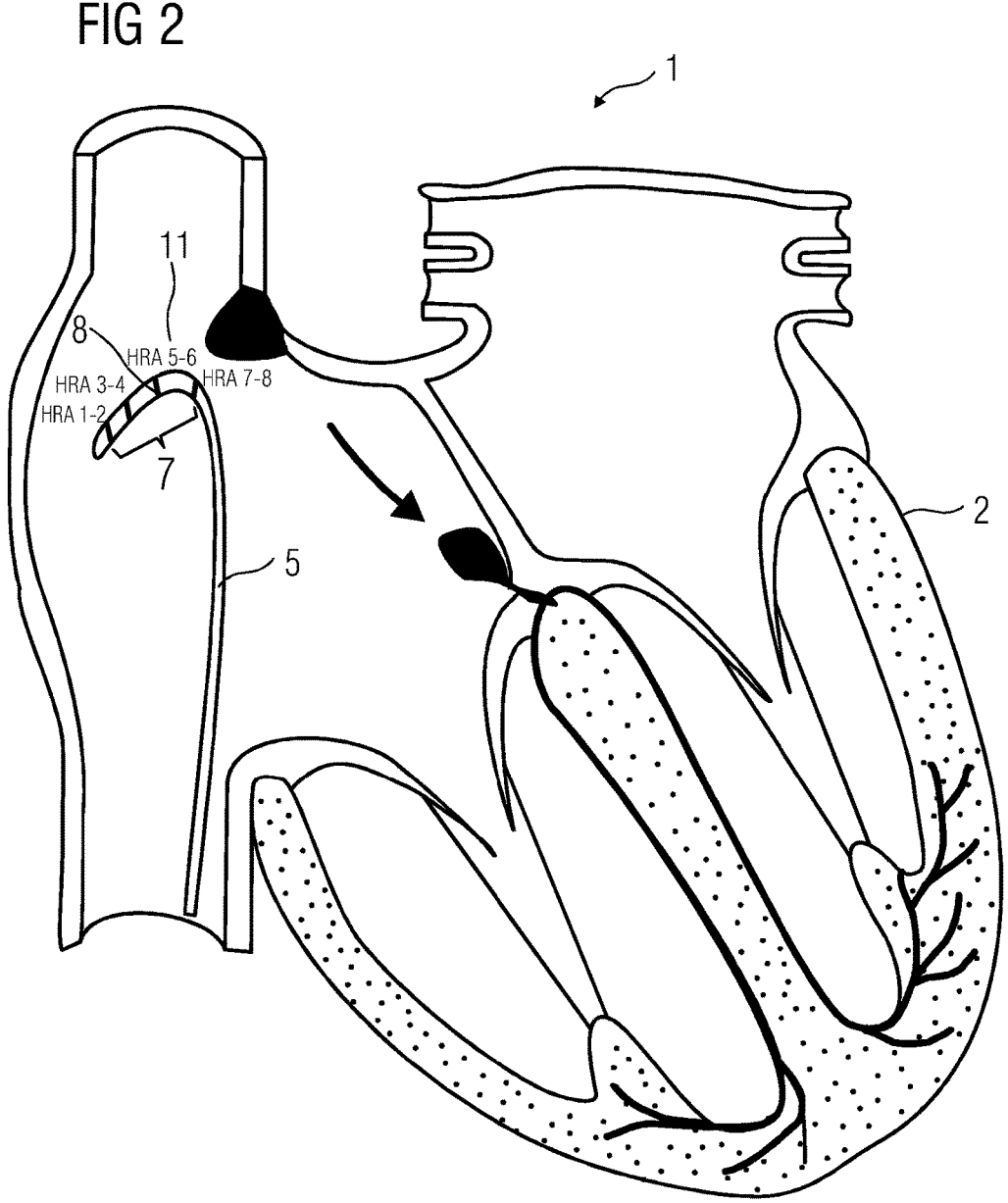

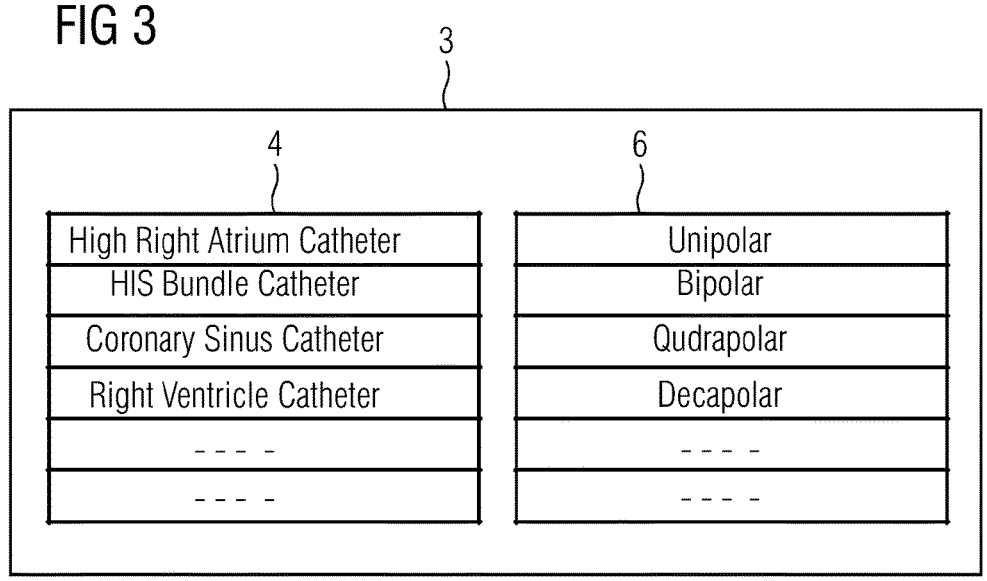
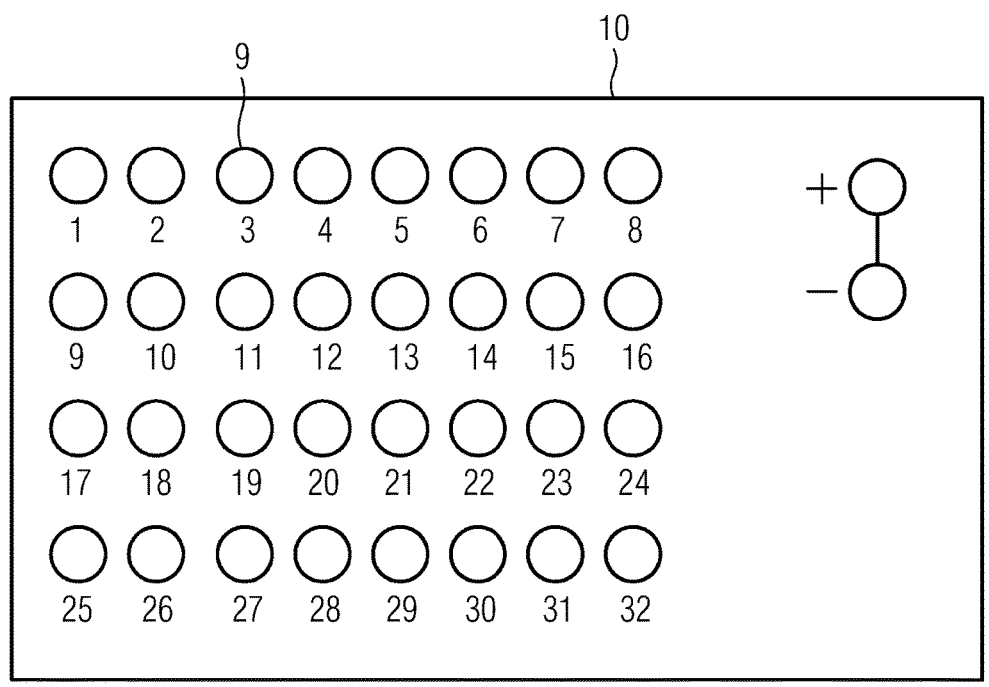

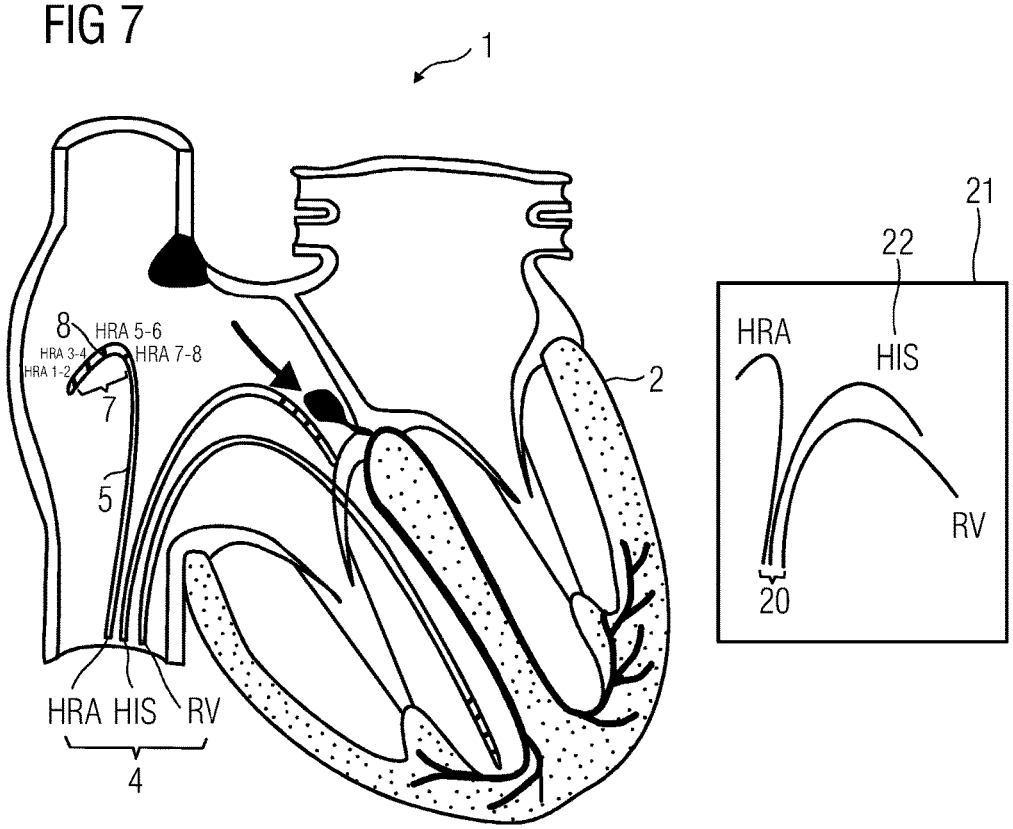

FIG 8B
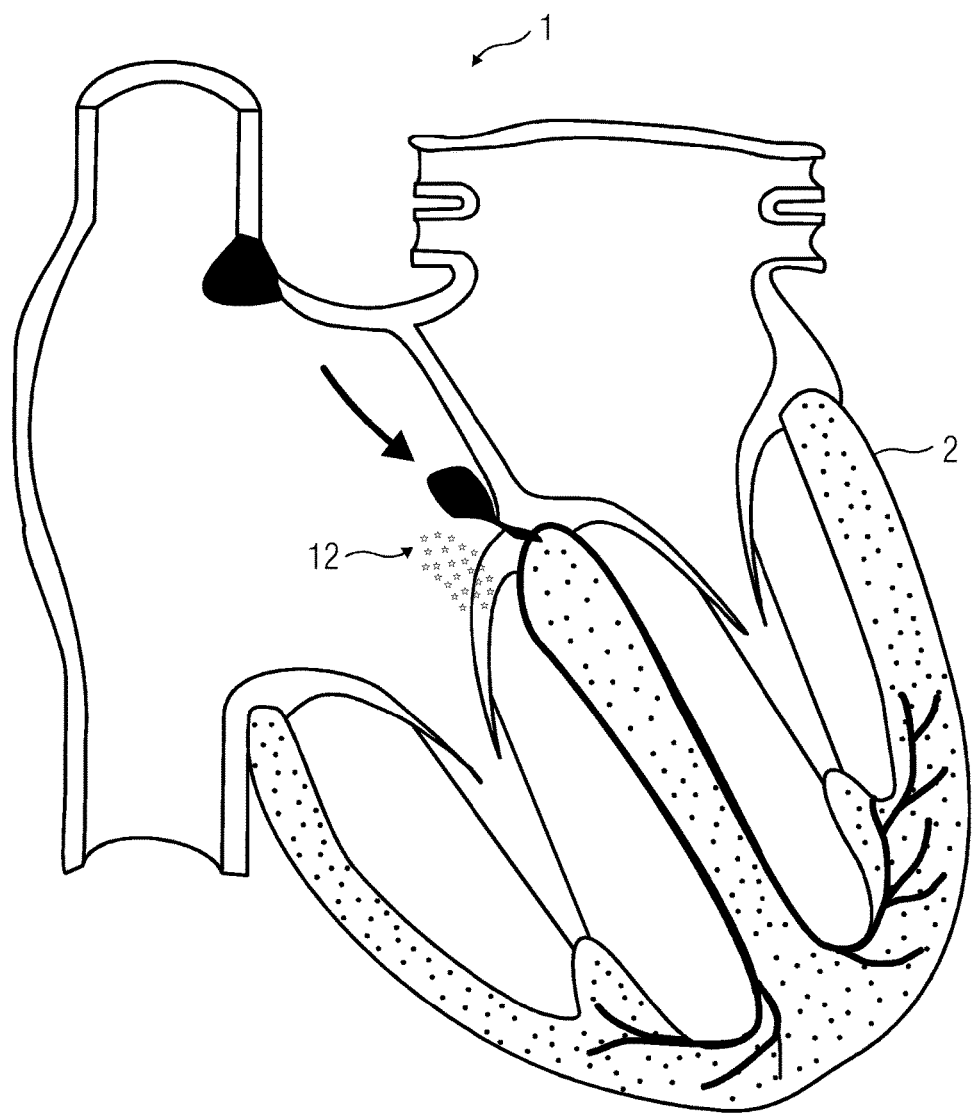
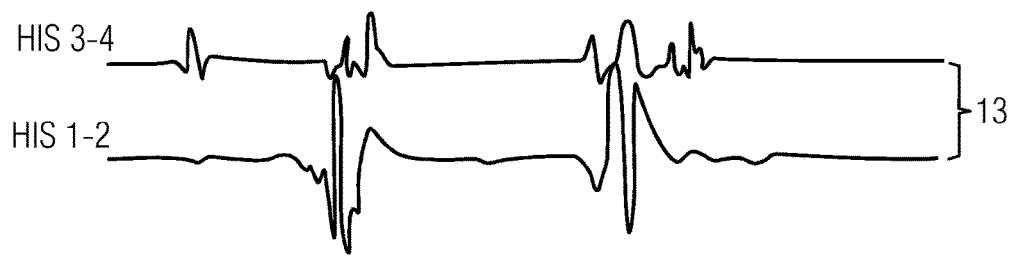

FIG 8C
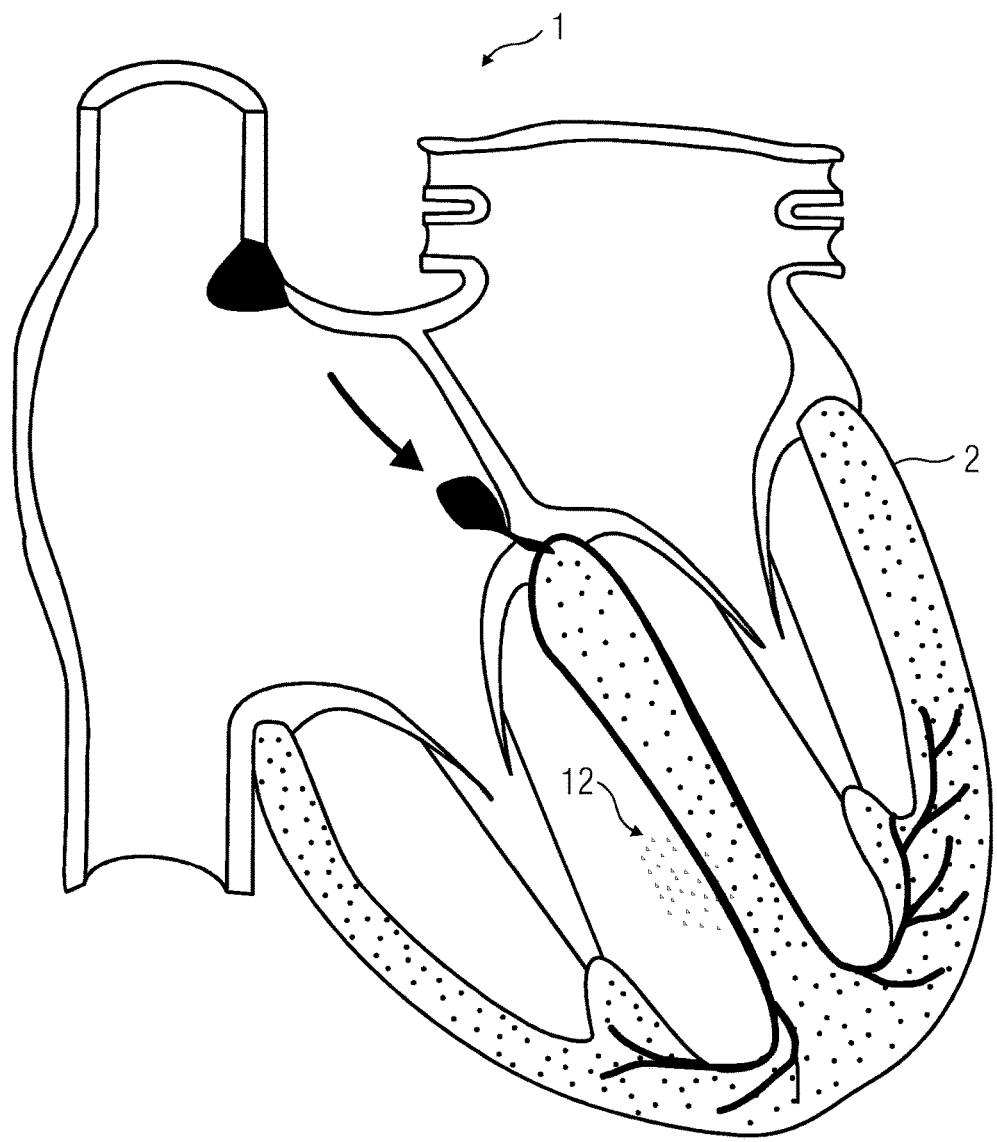
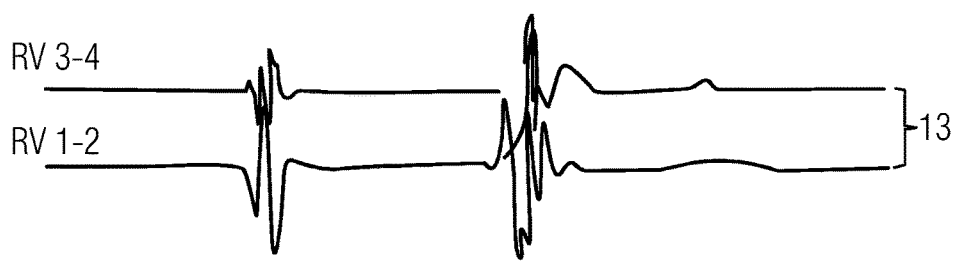

METHOD AND APPARATUS FOR ELECTROPHYSIOLOGY CATHETER SCHEME CONFIGURATION

FIELD OF TECHNOLOGY

The present embodiments relate to the field of electrophysiology catheter input configuration.

BACKGROUND

Heart supplies blood to the whole body by pumping the blood through a complex process of contraction and relaxation of heart muscles. The heart muscles are stimulated to contract by an electrical pulse generated by the sinoatrial node of the heart. This electrical pulse is propagated to the cardiac muscle, known as myocardium, and stimulates the myocardium to contract. It is the ordered stimulation of the myocardium that allows efficient contraction of the heart, thereby allowing blood to be pumped throughout the body.

When there is any irregularity in the generation of this electrical impulse, abnormalities arise in the functioning of the heart. To study and monitor these electrical pulses generated in the heart, electrophysiology catheters are used. Electrophysiology is the study of electrical properties of biological cells and tissues. Classical electrophysiology techniques involve placing electrodes into various preparations of biological tissue. For measuring the electrical impulse of the heart, catheters with electrodes are placed into the heart, and the pulses generated by the sinoatrial node are picked up by these electrodes and may be measured by a catheter input pod. The electrodes are connected to the slots of the catheter input pod, and the electrical signal received by each of the electrodes may be measured.

In typical electrophysiology (EP) studies, physicians place the EP catheters inside the heart of the patient, whose heart signals are to be monitored, and analyze the signals coming from various electrodes of the catheters. These EP catheters have multiple sensors to gauge the electric impulses at the location where sensors are placed. The sensor data may be received from the electrodes provided with catheters.

In most EP recording systems, an EP catheter scheme is to be created to read the EP catheter data. The EP catheter scheme creation involves configuring the EP catheter electrodes to the catheter input pod (CIP) interfaces with EP recording system hardware (e.g., in which slot of the CIP will the electrode be connected is to be determined). For example, for configuring a bipolar catheter that will be placed at the right ventricular (RV) site in the heart, the user selects the suitable nomenclature in the EP recording system interface that virtually represents two slots of the CIP. This indicates to the system that these two slots will be used by the RV catheters and is represented as RV: 1 and RV: 2.

This configuration alone will not allow the system to display the signals. The user also adds the ICEG signals, selecting RV:1 and RV:2 as +ve and −ve electrodes for the signal depending on the polarity of the bipolar RV catheter. Only now the ICEG signal may be used in the setup to display the signal when the EP examination starts.

However, for a single EP study, these steps are to be repeated a number of times for each catheter, and most of the studies will have more than 22 signals. This consumes a lot of time for the physician. A study may have a maximum of 64 signals (e.g., 128 electrodes). In the current EP catheter configuration systems, all the ICEG electrodes are configured manually using the EP catheter scheme available or preconfigured on the system and visible to the user through a dialog or interface. It is a time consuming task and prone to human errors.

U.S. Pat. No. 8,725,241 is relevant for this patent application. This patent provides a computer-implemented method including storing electroanatomic data representing electrical activity for a predetermined surface region of an organ of a patient in memory, and providing an interactive graphical representation of the predetermined surface region of the patient. A user input is received to define location data corresponding to a user-selected location for at least one virtual electrode on the graphical representation of the predetermined surface region of the patient. A visual representation of physiological data for the predetermined surface region of the patient is generated based on the location data and the electroanatomic data.

The above prior art discloses a method for post-processing of the information captured at a predetermined location by the virtual electrode and representing the physiological data graphically to a user. The prior art does not provide any way for easy configuration of EP catheter inputs. The prior art only provides a post processing operation on physiological data to give a graphical representation of such physiological data.

U.S. Pat. No. 8,382,706 B2 is another relevant piece of prior art. The patent provides a user interface system for catheter input management. The system includes a virtual catheter input module (CIM) corresponding to and representing a physical CIM that is adapted to be connected to at least one catheter. The system also includes a configuration module establishing a catheter configuration for the virtual CIM based on a plurality of configuration settings for a catheter channel. At least one catheter channel is assigned to a virtual input port on the virtual CIM. The configuration module applies the catheter configuration for at least one catheter channel when a catheter is connected to a physical input port on the physical CIM corresponding to the virtual input port on the virtual CIM.

The above prior art provides a catheter input management system where the user has to manually configure the catheters according to the catheter scheme that is virtually available. The prior art does not address the cumbersome problem of manual configuration of each catheter. The prior art only provides a virtual catheter scheme that the user uses to configure the catheters in a tedious manner physically.

SUMMARY AND DESCRIPTION

In light of the prior art described above, a need exists for a simple, user friendly and time saving method for electrophysiology (EP) catheter scheme configuration that does not require the user to configure EP catheters based on a complex virtual scheme available on a display.

The present embodiments may obviate one or more of the drawbacks or limitations in the related art. For example, an EP catheter scheme configuration method and an EP catheter scheme configuration device that make catheter configuration simpler by providing a visual representation of the heart to the user to enable easier configuration of catheters are provided. As another example, a graphical representation of the electrical stimulation of the heart for easier observation and analysis purposes is provided.

A method and an apparatus for electrophysiology catheter scheme configuration are disclosed. According to one embodiment, a method for electrophysiology catheter scheme configuration includes providing an interactive image of a heart to a user, and receiving a user input of a type of catheter and a number of electrodes corresponding to the catheter. A pictorial representation of the catheter positioned inside the interactive image of the heart is generated according to the type of catheter, and a pictorial representation of the electrodes as markers is generated on the pictorial representation of the catheter depending on the number of electrodes. Slot numbers of a catheter input pod are mapped to the corresponding electrodes of the catheter that are to be connected to the catheter input pod depending on the type of catheter. Intracardiac electrogram (ICEG) signal labels are assigned depending on the type of catheter, and the ICEG signal labels are marked on the interactive image of the heart to create the electrophysiology catheter scheme.

The electrophysiology catheter scheme includes the configuration of the various electrodes of catheters on the interactive image of the heart.

In one embodiment, the catheter position inside the interactive image of the heart is adjustable by the user. Once the user inputs the catheter type and the number of electrodes, the method generates a pictorial representation of the position of the catheters on the interactive image of the heart. Seeing the pictorial representation of the catheter positioned inside the interactive image of the heart, the user may adjust the parking or the position of the catheter if desired. For example, if the user feels that the right ventricle catheter should be placed further down into the right ventricular cavity of the heart, then the user has the option to move the catheter as desired. This helps the user to position and relocate the catheters based on the need of the examination.

In another embodiment of the method, the interactive image of the heart is in three dimensions. This helps the user to accurately visualize the real heart of the patient whose heart is being examined and estimate how the catheters are positioned in the real heart to a significant level of accuracy. A three dimensional image gives an almost life-like visualization of the real heart and reduces chances of error on the part of the user in mapping the heart of the patient to the interactive image of the heart and the corresponding catheter placement.

In yet another embodiment, the method includes saving the electrophysiology catheter scheme. This will help in referring to the electrophysiology catheter scheme for a different study with a similar medical case or for analysis by the physician at any later point of time.

In an embodiment of the present method, the pictorial representation of the catheter is represented by a distinct color for each type of catheter. For example, the pictorial representation of the catheter placed in the right ventricle of the heart is represented by the color green in the interactive image of the heart, and the pictorial representation of the catheter placed in the high right atrium of the heart is represented by the color pink in the interactive image of the heart. This will help the physician to easily differentiate between various catheters. This is more useful when there are several catheters simultaneously placed inside the heart. By using different color codes for the catheters, the user need not always look up the catheter names when analyzing the image. This will save time and reduce the chances of error during the electrophysiology examination.

In yet another embodiment, the mapping of the slot numbers of the catheter input pod to the corresponding electrodes is reconfigurable by the user. The user may change the configuration of the electrodes in the catheter input pod and reconfigure the electrodes if a different configuration is preferred. Therefore, the configuration is flexible and does not bind the user to a fixed configuration. If the user wishes to space out the electrode configuration by choosing the slots far apart from each other, the provision of reconfigurable mapping of electrodes to the slots of the catheter input pod may provide this.

According to a further embodiment of the method, the method includes tilting the interactive image of the heart as per a configured x-ray position to compare the catheter positioned inside the interactive image of the heart with a real catheter placed inside a heart of a patient, where the real catheter is visible on an x-ray image of the heart of the patient. The x-ray image is captured in the configured x-ray position. This helps the physician in the EP study to compare the x-ray images of the real catheters with the catheters visible in the interactive image of the heart. By tilting the interactive image according to the x-ray position (e.g., Left Anterior Oblique (LAO) position or Right Anterior Oblique (RAO) position), the user may view the catheters from the same angle as the angle in the x-ray image.

In yet another embodiment, the method further includes assigning labels on the x-ray image based on the electrophysiology catheter scheme. The advantage of having labels assigned on the x-ray image will make it easier for the physician to study the x-ray image with more comfort, and the assigned labels increase the readability and comprehension of the x-ray image. The user need not spend time trying to figure out which catheter is shown on the x-ray image. The user may check the label assigned to the catheter shown on the x-ray image.

According to an embodiment of the method, the method includes simulating electricity conduction along the electrodes corresponding to the catheter based on electric pulses observed on ICEG signals. This feature provides a visual aid to the physician by depicting the electrical signal flow direction through the electrodes in the interactive image of the heart. In cases when there is an abnormal heart condition and the electrical stimulation of the myocardium is irregular, the flow of the electrical signal through the heart will also be irregular. The electrical signal as picked up by the various electrodes on the catheters is visually depicted on the interactive image of the heart, and the physician may check the flow of the electrical signal by observing the simulation of electricity conduction along the electrodes and easily determine when the flow is irregular or obstructed.

According to a further embodiment, the simulation of the electricity conduction along the electrodes is represented by a distinct color for each type of catheter. This makes it easier for the physician to analyze the electricity conduction for each catheter distinctly and removes any confusion when there are multiple catheters simultaneously being observed for the simulation of the electricity conduction.

In a further embodiment, the electrophysiology catheter scheme is usable for creating electrophysiology set ups. The physician may use the same configuration for future EP examinations and need not start the steps all over again. This will save time for the physician when a similar medical examination, which uses the same type of catheters, number of electrodes and the catheter positioning, is to be performed.

In yet another embodiment, a non-transitory computer-readable storage medium having machine-readable instructions stored therein is provided. When the machine-readable instructions are executed by a processor, the processor is caused to execute an electrophysiology catheter scheme, as described above.

According to an embodiment of the apparatus, the apparatus for electrophysiology catheter scheme configuration includes, for example, a communication interface, a display unit, a processor and a memory unit. The communication interface is configured for receiving user input. The user input includes data representing a type of catheter and a number of electrodes corresponding to the catheter. The display unit is coupled to the communication interface for displaying a pictorial representation of the catheter positioned inside an interactive image of a heart according to the type of catheter received from the user as input, and for displaying a pictorial representation of the electrodes as markers on the pictorial representation of the catheter depending on the number of electrodes received as an input from the user. The processor, which is coupled to the communication interface, creates the electrophysiology catheter scheme. The memory unit, which is coupled to the processor, saves the electrophysiology catheter scheme.

According to a further embodiment of the apparatus, the processor creates the electrophysiology catheter scheme by mapping slot numbers of a catheter input pod to the corresponding electrodes of the catheter that are to be connected to the catheter input pod depending on the type of catheter, assigning ICEG signal labels depending on the type of catheter, and marking the ICEG signal labels on the interactive image of the heart.

According to yet another embodiment of the apparatus, the memory unit further includes a storage unit.

This summary is provided to introduce a selection of concepts in a simplified form that are further described below in the following description. The summary is not intended to identify features or essential features of the claimed subject matter. The claimed subject matter is not limited to implementations that solve any or all disadvantages noted in any part of this disclosure.

BRIEF DESCRIPTION OF THE DRAWINGS

FIG. 1 illustrates an embodiment of a method for electrophysiology catheter scheme configuration;

FIG. 2 illustrates a schematic diagram of an exemplary electrophysiology catheter scheme configuration on the interactive image of the heart;

FIG. 3 illustrates exemplary user input options available to a user;

FIG. 4 illustrates an exemplary catheter input pod with slots;

FIG. 7 illustrates an exemplary catheter scheme configuration on the interactive image of the heart with regard to the x-ray image containing multiple catheters;

FIGS. 8A, 8B and 8C depict a schematic representation of an exemplary simulation of electricity conduction along the electrodes of the catheter;

DETAILED DESCRIPTION

Figure 5:
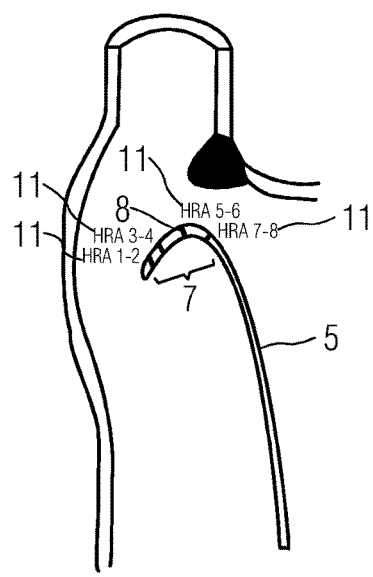
FIG. 5 illustrates an exemplary intracardiac electrogram (ICEG) signal labeling on the pictorial representation of the catheter in the interactive image of the heart.

A method 100 and an apparatus 30 for electrophysiology catheter scheme configuration 1 are disclosed. Various embodiments are described with reference to the drawings, wherein like reference numerals are used as in reference to the drawings. Like reference numerals are used to refer to like elements throughout. In the following description, numerous specific details are set forth in order to provide thorough understanding of embodiments of the present disclosure. It will be apparent, however, to one skilled in the art, that these specific details need not be employed to practice embodiments of the present disclosure. In other instances, well known materials or methods have not been described in detail in order to avoid unnecessarily obscuring embodiments of the present disclosure. While the disclosure is susceptible to various modifications and alternative forms, specific embodiments thereof are shown by way of example in the drawings and will herein be described in detail. There is no intent, however, to limit the disclosure to the particular forms disclosed. The disclosure is to cover all modifications, equivalents, and alternatives falling within the spirit and scope of the present disclosure.

FIG. 1 illustrates a flowchart depicting the various acts in the method 100 to be carried out for electrophysiology catheter scheme 1 configuration. The method 100 includes act 101 of providing an interactive image 2 of a heart (see FIG. 2) to a user. The user is able to see the interactive image 2 and accordingly provide inputs 3 (see also FIG. 2). This forms act 102 of the method 100. The user input 3 includes a type 4 of catheter 5 and a number 6 of electrodes 7 corresponding to the catheter 5. The act 103 includes generating a pictorial representation of the catheter 5 positioned inside the interactive image 2 of the heart according to the type 4 of catheter 5 and also generating a pictorial representation of the electrodes 7 (see FIG. 2) as markers 8 on the pictorial representation of the catheter 5 depending on the number 6 of electrodes 7. The act 104 involves mapping slot 9 (see FIG. 4) numbers of a catheter input pod 10 to the corresponding electrodes 7 of the catheter 5 that are to be connected to the catheter input pod 10 depending on the type 4 of catheter 5. In act 105, intracardiac electrogram (ICEG) signal labels 11 are assigned depending on the type 4 of catheter 5. The act 106 includes marking the ICEG signal labels 11 on the interactive image 2 of the heart to create the electrophysiology catheter scheme 1.

FIG. 2 illustrates a schematic diagram of the electrophysiology catheter scheme 1 configuration on the interactive image 2 of the heart. The interactive image 2 of the heart is visible to the user. On seeing the interactive image 2, the user selects the choice of catheter 5 type 4 and the number 6 of electrodes 7 for each catheter type 4 selected and feeds in these user input 3 choices. These user input 3 choices reflect on the interactive image 2 of the heart. For example, the user has chosen a catheter 5 for the right ventricle, denominated as RV catheter. If the user desires the RV catheter 5 to have four electrodes 7, then the user selects quadrapolar as an option for the number 6 of electrodes 7. The interactive image 2 of the heart then displays a pictorial representation of the RV catheter 5 placed inside the right ventricle of the interactive image 2 of the heart. The four electrodes 7 are pictorially represented by markers 8 on the pictorial representation of the RV catheter 5. Thus, the user is able to see the selection of the user in visual representation.

FIG. 2 also depicts the ICEG signal label 11 as marked on the catheter 5. The ICEG signal labels 11 are assigned to the markers 8 of the electrodes 7 based on the proximal distance of the electrode 7 from the sinoatrial node of the heart. The closer the electrode 7 is to the sinoatrial node the higher the ICEG signal label 11 assigned to the electrode 7 will be. This will be discussed at length below with reference to FIG. 5.

FIG. 3 shows exemplary user input 3 options available to the user. The user input 3 includes at least two selections to be made by the user. The first selection to be made is the type 4 of the catheter 5 to be used in the EP study. The second selection that forms a part of the user input 3 is the number 6 of electrodes 7 for the corresponding catheter 5. Therefore, the user keys in the selections of a catheter type 4 and a corresponding electrode number 6 for the catheter 5. The options are displayed to the user for easier selection.

FIG. 3 shows an exemplary list of options available to the user. The type 4 of catheter 5 may be any one of the listed types 4 according to FIG. 3 (e.g., High Right Atrium catheter, HIS Bundle catheter, Coronary Sinus catheter, Right Ventricle catheter etc.). Any other type 4 of catheters 5 that are used in EP examination and studies may also be listed. The number 6 of electrodes 7 may be specified as unipolar for a single electrode, bipolar for two electrodes, quadrapolar for four electrodes, decapolar for ten electrodes, and so on.

FIG. 4 shows an exemplary catheter input pod 10. The catheter input pod 10 is a device to which the input from the catheter electrode 7 is connected for measuring an electrical signal that is sensed by the electrode 7. The exemplary catheter input pod 10 according to FIG. 4 has thirty two slots 9 for receiving catheter 5 inputs. In an EP examination, at one time, the user may use only a few slots 9 depending on the number 6 of electrodes 7 chosen for each catheter 5 being used in the examination. The users are free to select any individual slot 9 for an individual electrode 7. For example, for a high right atrium (HRA) bipolar catheter, the ICEG signal label HRA1-2 may be configured at third and fourth slots 9 of the catheter input pod 10, and the ICEG signal label HRA 3-4 may be configured at tenth and eleventh slots 9 etc. of the catheter input pod 10.

The user may change the configuration of the electrodes 7 in the catheter input pod 10 as desired (e.g., the physician is free to shift the electrode 7 selection). For example, if a high right atrium (HRA) quadrapolar catheter is using the first eight slots 9 of the catheter input pod 10, the physician may select all the four electrodes and move to right or down, and the electrode slots are assigned depending on where the first slot 9 label is positioned. For example, if first electrode 7 input slot 9 is moved to third slot 9 position, then the electrodes get assigned to slots 9 that lie subsequently from the third slot 9 position (e.g., slots 9 from third to tenth positions are used).

FIG. 5 illustrates an exemplary labeling of ICEG signal labels 11 on the pictorial representation of the catheter 5 in the interactive image 2 of the heart. The catheter 5 shown in FIG. 5 is a high right atrium (HRA) catheter 5, and four markers 8 on the HRA catheter 5 represent the electrodes 7. The ICEG signal labels 11 are assigned to the electrodes 7 on the catheter 5, as shown in FIG. 5, starting from HRA1-2 up to HRA7-8 for a quadrapolar electrode for the HRA catheter 5 having four electrodes 7. The sequence of the ICEG signal label 11 depends on the proximity of the electrode 7 to the sinoatrial node of the heart. The electrode 7 that is farthest from the sinoatrial node is labeled with the lowest denomination (e.g., HRA1-2 (distal)). The electrode 7 that is closest to the sinoatrial node is labeled with the highest denomination (e.g., HRA7-8 (proximal) for a quadrapolar HRA catheter).

Similarly, if a unipolar catheter 5 is chosen, then the ICEG signal label 11 for the HRA catheter 5 may be HRA1-2. FIG. 5 displays only an exemplary ICEG signal label 11, and depending on the catheter 5 type 4 and the number 6 of electrodes 7 of the catheter 5, the ICEG signal labels 11 on the interactive image 2 of the heart would change. For example, for a HIS bundle (HIS) quadrapolar catheter 5, the ICEG signal label 11 suggested on the interactive image 2 of the heart would be HIS1-2 (distal), HIS3-4, HIS5-6, HIS7-8 (proximal).

For coronary sinus (CS) decapolar catheter 5, the ICEG signal label 11 would be, for example, CS1-2 (distal), CS3-4, CS5-6, CS7-8, CS9-10 (proximal). Similarly, for right ventricle (RV) quadrapolar catheter 5, the ICEG signal label 11 would be, for example, RV1-2 (distal), RV3-4, RV5-6, RV7-8 (proximal). Thus, the ICEG signal labels 11 depend on the catheter type 4, the number 6 of electrodes 7 and the proximity of the electrode 7 from the sinoatrial node of the heart.

Figure 6:
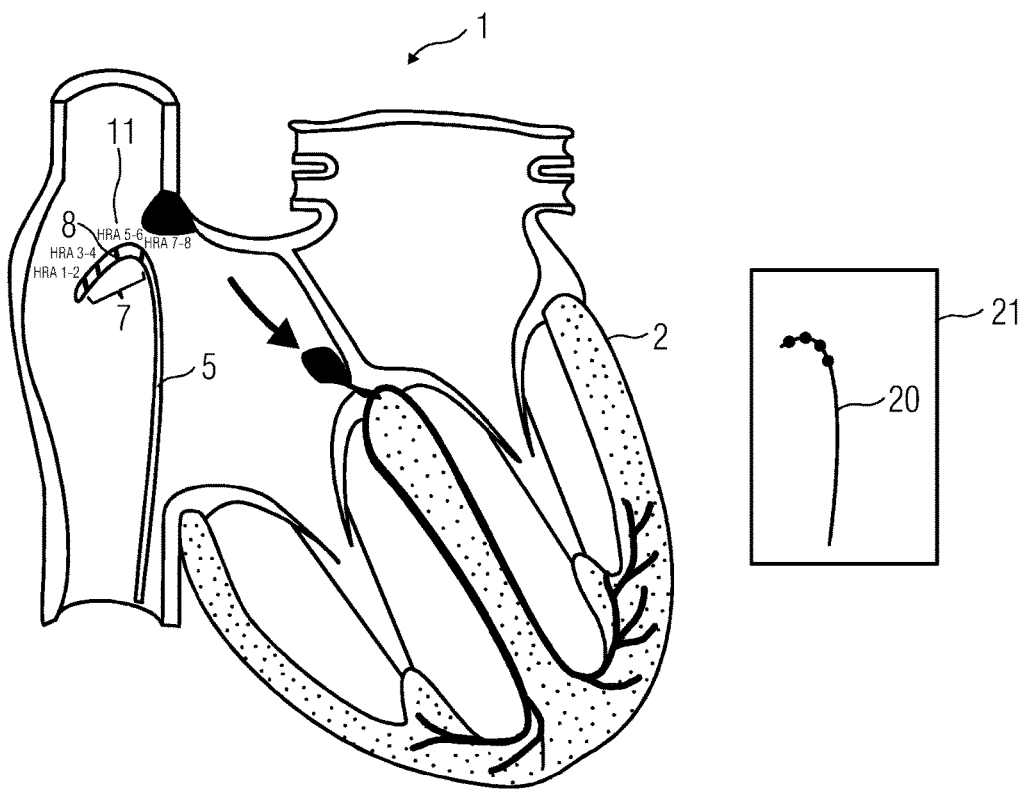
FIG. 6 illustrates a schematic representation of an exemplary electrophysiology catheter scheme configuration on the interactive image of the heart with regard to the x-ray image depicting the catheter position in the heart of a patient.

FIG. 6 illustrates a schematic representation of the electrophysiology catheter scheme 1 configuration on the interactive image 2 of the heart with regard to the x-ray image 21 depicting the catheter 5 position in the heart of a patient. The interactive image 2 of the heart displays a virtual representation of the catheter 5 placed inside a virtual image of the heart. This virtual image or the interactive image 2 of the heart may, however, be compared to a real heart of a patient, inside which a real catheter 20 has been placed by a physician. An x-ray image 21 of the heart of the patient that shows the position of the real catheter 20 inside the heart is taken. This x-ray image 21 may be viewed simultaneously with the interactive image 2 of the heart, and the position of the catheter 5 inside the interactive image 2 of the heart may be adjusted to match the real catheter 20 position inside the heart of the patient as visible on the x-ray image 21.

FIG. 7 is a schematic representation depicting electrophysiology catheter scheme 1 configuration on the interactive image 2 of the heart with regard to the x-ray image 21 containing multiple real catheters 20. FIG. 7 shows the interactive image 2 of the heart, wherein three catheters 5 have been parked inside the heart. The first catheter 5 is of the type 4 high right atrium (HRA) catheter 5, the second catheter 5 is of the type 4 HIS bundle (HIS) catheter 5, and the third catheter 5 is of the type 4 right ventricle (RV) catheter 5. Each of the three catheters 5 has four electrodes 7. The x-ray image 21 depicts the real catheters 20 placed in the heart of the patient. The x-ray image of the real catheters 20 seen in the x-ray image 21 may be mapped to the pictorial representation of the respective catheters 5 seen in the interactive image 2 of the heart.

Sometimes it is difficult to map the catheters 5 as seen in the interactive image 2 of the heart to the real catheters 20 visible in the x-ray image 21. For this reason, the feature of assigning labels 22 to the catheters 20 on the x-ray image 21 is provided. This will help the physician to easily identify one real catheter 20 from the other in the x-ray image 21 (e.g., in cases where there are multiple real catheters 20 being used).

Figure 8A:
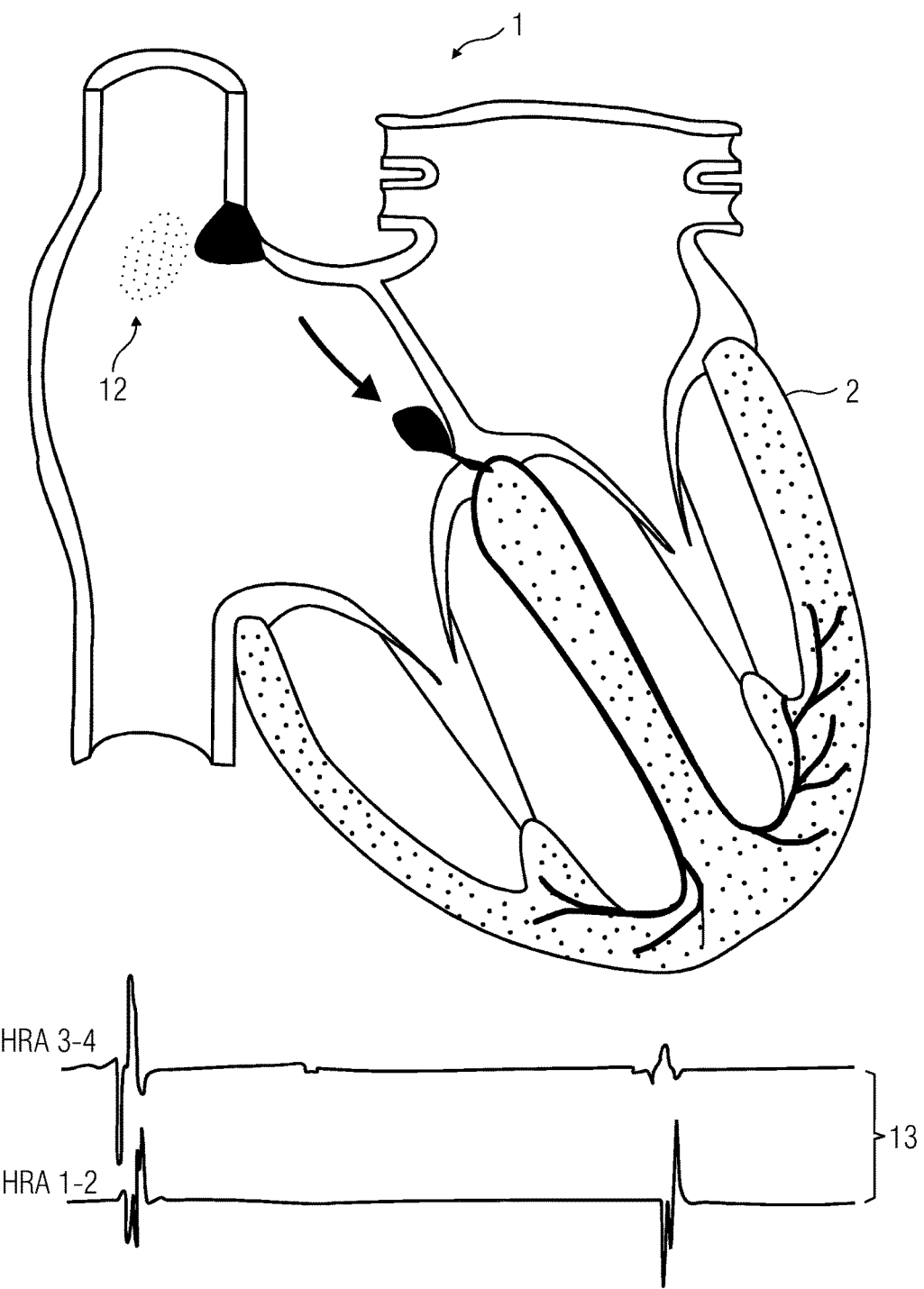

FIGS. 8A, 8B and 8C depict a schematic representation of an exemplary simulation of electricity conduction 12 along the electrodes 7 of the catheter 5 on the interactive image 2 of the heart. Depending on the type 4 of catheters 5 placed in the heart, the interactive image 2 of the heart, as shown in FIG. 8A, simulates the electricity conduction 12 along the electrodes 7 of the catheter 5 based on electric pulses observed on ICEG signals. The waveform of electric pulse 13 for the corresponding catheter 5 is also shown.

For example, as shown in FIG. 8A, if the high right atrium (HRA) bipolar catheter 5 receives electricity signal, the interactive image 2 of the heart displays a pictorial representation of electricity. In one embodiment, the pictorial representation of the electricity is made by a distinct color for each type 4 of catheter 5. For example, for HRA catheter 5, the simulation of electricity conduction 12 is shown by red color on the interactive image 2 of the heart. The electric pulse sensed by the HRA catheter 5 is shown by the waveform for the electric pulse 13.

In FIG. 8B, HIS bundle (HIS) catheter 5 is shown to be conducting electricity. The pictorial representation for simulation electricity conduction 12 for HIS catheter 5 may be shown by another color, which is distinguishable from the color used for HRA catheter 5 (e.g., blue). The electric pulse sensed by the HIS catheter 5 is shown by the waveform for the electric pulse 13.

In FIG. 8C, right ventricle (RV) catheter 5 is shown to be conducting electricity. The pictorial representation for simulation of electricity conduction 12 for RV catheter 5 may be shown by yet another different color (e.g., green). The electric pulse sensed by the RV catheter 5 is shown by the waveform for the electric pulse 13. Any other color for depicting simulation of electricity conduction 12 for different types 4 of catheters 5 may be used as desired. In a further embodiment, the direction of the electricity flow may also be shown on the interactive image 2 of the heart.

Figure 9:
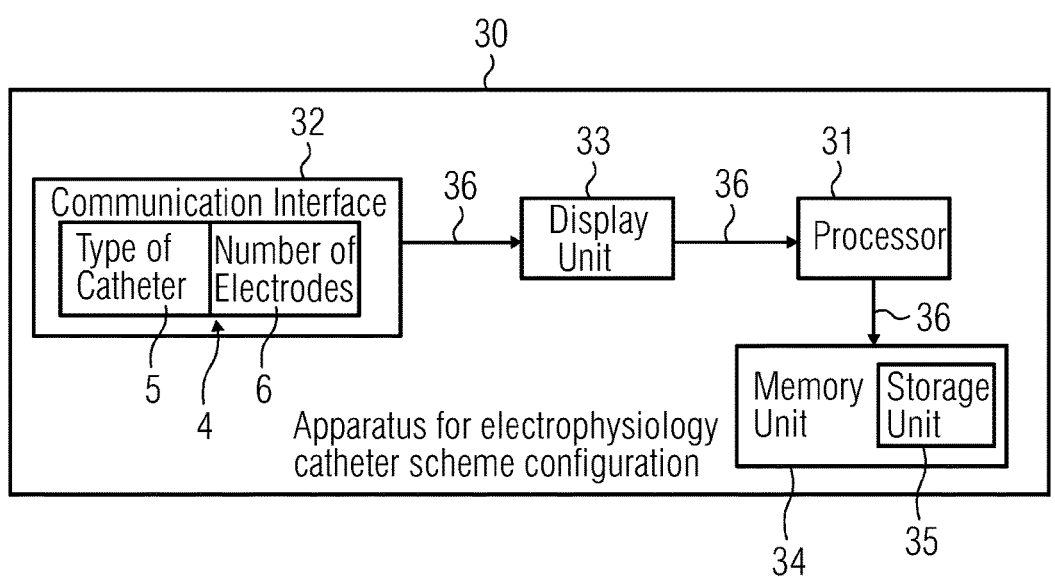
FIG. 9 illustrates a block diagram of one embodiment of an apparatus for electrophysiology catheter scheme configuration.

FIG. 9 illustrates a block diagram of one embodiment of the apparatus 30 for carrying out the method 100 for electrophysiology catheter scheme 1 configuration. The apparatus 30 may be a personal computer, a laptop computer, a tablet, a health monitoring device and the like. In FIG. 9, the apparatus 30 includes a processor 31, a communication interface 32, a display unit 33, a memory unit 34, a storage unit 35 and a bus 36.

The processor 31, as used herein, may be any type of computational circuit, such as, but not limited to, a microprocessor, microcontroller, complex instruction set computing microprocessor, reduced instruction set computing microprocessor, very long instruction word microprocessor, explicitly parallel instruction computing microprocessor, graphics processor, digital signal processor, or any other type of processing circuit. Processor 31 may also include embedded controllers, such as generic or programmable logic devices or arrays, application specific integrated circuits, single-chip computers, and the like.

Memory unit 34 may be volatile memory and non-volatile memory. The memory unit 34 may be coupled for communication with processor 31. Processor 31 may execute instructions and/or code stored in the memory unit 34. A variety of computer-readable storage media may be stored in and accessed from the memory unit 34. The memory unit 34 may include any suitable elements for storing data and machine-readable instructions, such as read only memory, random access memory, erasable programmable read only memory, electrically erasable programmable read only memory, a hard drive, a removable media drive for handling compact disks, digital video disks, diskettes, magnetic tape cartridges, memory cards, and the like. In the present embodiment, the memory unit 34 includes a storage unit 35.

The storage unit 35 may be a non-transitory storage medium that stores the electrophysiology catheter scheme 1 configuration. The communication interface 32 enables the apparatus 30 to communicate with the user to receive the inputs 3. The communication interface 32 may include an input device such as a keypad, a touch-sensitive display, etc. capable of receiving inputs 3. The bus 36 acts as an interconnect between the processor 31, the communication interface 32, the display unit 33 and the memory unit 34.

It is to be understood that the system and methods described herein may be implemented in various forms of hardware, software, firmware, special purpose processors, or a combination thereof. One or more of the present embodiments may take a form of a computer program product including program modules accessible from computer-usable or computer-readable medium storing program code for use by or in connection with one or more computers, processors, or instruction execution system. For the purpose of this description, a computer-usable or computer-readable medium may be any apparatus that may contain, store, communicate, propagate, or transport the program for use by or in connection with the instruction execution system, apparatus, or device. The medium may be an electronic, magnetic, optical, electromagnetic, infrared, or semiconductor system (or apparatus or device). Propagation mediums in and of themselves as signal carriers are not included in the definition of physical computer-readable medium. The medium may include a semiconductor or solid state memory, magnetic tape, a removable computer diskette, random access memory (RAM), a read only memory (ROM), a rigid magnetic disk and optical disk such as compact disk read-only memory (CD-ROM), compact disk read/write, and/or DVD. Both processors and program code for implementing each aspect of the technology may be centralized or distributed (or a combination thereof) as known to those skilled in the art.

While the present disclosure has been described in detail with reference to certain embodiments, the present disclosure is not limited to these embodiments. In view of the present disclosure, many modifications and variations would be present to those skilled in the art without departing from the scope of the various embodiments of the present disclosure, as described herein. The scope of the present disclosure is, therefore, indicated by the following claims rather than by the foregoing description. All changes, modifications, and variations coming within the meaning and range of equivalency of the claims are to be considered within their scope.

The invention claimed is:

1. A method for electrophysiology catheter scheme configuration, the method comprising:
   providing, by a processor, an interactive image of a heart to a user;
   receiving, by the processor, a user input of a type of catheter and a number of electrodes corresponding to the catheter;
   generating, by the processor, a pictorial representation of the catheter positioned inside the interactive image of the heart according to the received user input of the type of catheter and generating a pictorial representation of the electrodes as markers on the pictorial representation of the catheter depending on the number of electrodes according to the received user input;
   mapping, by the processor, slot numbers of a catheter input pod to the corresponding electrodes of the catheter that are to be connected to the catheter input pod depending on the type of catheter;
   assigning, by the processor, intracardiac electrogram (ICEG) signal labels to the corresponding electrodes of the catheter depending on the type of catheter received as the user input; and
   marking, by the processor, the ICEG signal labels on the interactive image of the heart.

2. The method of claim 1, wherein the electrophysiology catheter scheme comprises configuration of the electrodes of the catheter on the interactive image of the heart.

3. The method of claim 1, wherein the catheter positioned inside the interactive image of the heart is adjustable by the user.

4. The method of claim 1, wherein the interactive image of the heart is in three dimensions.

5. The method of claim 1, further comprising saving, by the processor, the electrophysiology catheter scheme.

6. The method of claim 1, wherein the pictorial representation of the catheter is represented by a distinct color for each type of catheter.

7. The method of claim 1, wherein the mapping of the slot numbers of the catheter input pod to the corresponding electrodes is reconfigurable by the user.

8. The method of claim 1, further comprising tilting, by the processor, the interactive image of the heart as per a configured x-ray position to compare the catheter positioned inside the interactive image of the heart with a real catheter placed inside a heart of a patient,
wherein the real catheter is visible on an x-ray image of the heart of the patient, and
wherein the x-ray image is captured in the configured x-ray position.

9. The method of claim 8, further comprising assigning, by the processor, labels on the x-ray image based on the electrophysiology catheter scheme.

10. The method of claim 1, further comprising simulating, by the processor, electricity conduction along the electrodes corresponding to the catheter based on electric pulses observed on ICEG signals.

11. The method of claim 10, wherein the simulation of the electricity conduction along the electrodes is represented by a distinct color for each type of catheter.

12. The method of claim 1, wherein the electrophysiology catheter scheme is usable for creating electrophysiology set ups.

13. A non-transitory computer-readable storage medium storing machine-readable instructions executable by a processor for electrophysiology catheter scheme configuration, the machine-readable instructions comprising:
providing an interactive image of a heart to a user;
receiving a user input of a type of catheter and a number of electrodes corresponding to the catheter;
generating a pictorial representation of the catheter positioned inside the interactive image of the heart according to the received user input of the type of catheter and generating a pictorial representation of the electrodes as markers on the pictorial representation of the catheter depending on the number of electrodes according to the received user input;
mapping slot numbers of a catheter input pod to the corresponding electrodes of the catheter that are to be connected to the catheter input pod depending on the type of catheter;
assigning intracardiac electrogram (ICEG) signal labels to the corresponding electrodes of the catheter depending on the type of catheter received as the user input; and
marking the ICEG signal labels on the interactive image of the heart.

14. An apparatus for electrophysiology catheter scheme configuration, the apparatus comprising:
a communication interface configured for receiving a user input, wherein the user input comprises data representing a type of catheter and a number of electrodes corresponding to the catheter;
a display unit coupled to the communication interface, the display unit operable to display a pictorial representation of the catheter positioned inside an interactive image of a heart according to the type of catheter received as the user input, and operable to display a pictorial representation of the electrodes as markers on the pictorial representation of the catheter depending on the number of electrodes received as the user input;
a processor coupled to the communication interface, wherein the processor is configured to create the electrophysiology catheter scheme; and
a memory unit coupled to the processor, the memory operable to save the electrophysiology catheter scheme,
wherein the creation of the electrophysiology catheter scheme comprises the processor being configured to:
map slot numbers of a catheter input pod to the corresponding electrodes of the catheter that are to be connected to the catheter input pod depending on the type of catheter;
assign intracardiac electrogram (ICEG) signal labels to the corresponding electrodes of the catheter depending on the type of catheter received as the user input; and
mark the ICEG signal labels on the interactive image of the heart.

15. The apparatus of claim 14, wherein the memory unit further comprises a storage unit.

* * * * *